US006395273B1

(12) United States Patent
Kink et al.

(10) Patent No.: US 6,395,273 B1
(45) Date of Patent: May 28, 2002

(54) PREVENTION AND TREATMENT OF INFLAMMATORY BOWEL DISEASE

(75) Inventors: John A. Kink; Katherine L. Worledge; Douglas C. Stafford, all of Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/095,535

(22) Filed: Jun. 10, 1998

(51) Int. Cl.$^7$ .................. A61K 39/395; A61K 39/00; C07K 16/00; C07K 16/07

(52) U.S. Cl. ................ 424/145.1; 424/139.1; 424/157.1; 424/158.1; 424/810; 424/436; 424/435; 424/464; 530/387.9; 530/387.1; 530/853; 530/861

(58) Field of Search ............... 424/145.1, 139.1, 424/157.1, 158.1, 810, 436, 435, 464; 530/388.23, 389.2, 853, 861

(56) References Cited

U.S. PATENT DOCUMENTS

| | | | |
|---|---|---|---|
| 4,477,432 A | 10/1984 | Hardie | 424/85 |
| 4,676,982 A | 6/1987 | Hassig | 424/85 |
| 4,677,064 A | 6/1987 | Mark et al. | 435/68 |
| 4,748,018 A | * 5/1988 | Stolle et al. | 424/157.1 |
| 4,870,163 A | 9/1989 | Rubin et al. | 530/43 |
| 5,080,895 A | 1/1992 | Tokoro | 424/85.8 |
| 5,385,901 A | 1/1995 | Kaplan et al. | 514/231.5 |
| 5,420,253 A | 5/1995 | Emery et al. | 530/423 |
| 5,436,154 A | 7/1995 | Barbanti et al. | 435/240.27 |
| 5,487,984 A | 1/1996 | Allet et al. | 435/69.5 |
| 5,604,231 A | 2/1997 | Smith et al. | 514/256 |
| 5,614,540 A | 3/1997 | Christensen | 514/362 |
| 5,654,407 A | 8/1997 | Boyle et al. | 530/388.15 |
| 5,656,272 A | 8/1997 | Le et al. | 424/133.1 |
| 5,672,347 A | 9/1997 | Aggarwal et al. | 424/139.1 |
| 5,707,622 A | 1/1998 | Fong et al. | 424/145.1 |
| 5,753,228 A | 5/1998 | Sterling et al. | 424/151.1 |
| 5,772,999 A | 6/1998 | Greenblatt et al. | 424/187.1 |
| 5,795,967 A | 8/1998 | Aggarwal et al. | 530/388.23 |

FOREIGN PATENT DOCUMENTS

| | | |
|---|---|---|
| EP | 0 155 549 B1 | 3/1991 |
| WO | WO96/33204 | 10/1996 |
| WO | WO97/15327 | 5/1997 |
| WO | WO98/14209 | 4/1998 |
| WO | WO 9814209 * | 4/1998 |

OTHER PUBLICATIONS

Polson et al., "Antibodies to Proteins from Yolk of Immunized Hens,"*Immunol. Comm.*, 9:495–514 (1980).

Okayasu et al., "A Novel Method in the Induction of Reliable Experimental Acute and Chronic Ulcerative Colitis in Mice," *Gastroenterology*, 98:694–702 (1990).

Kojouharoff et al.,"Neutralization of tumor necrosis facto (TNF) but not of IL–1 reduces inflammation in chronic dextran sulphate sodium–induced colitis in mice," *Clin. Exp.Immunology*, 107: 353–358 (1997).

Olson et al.,"Antiserum to Tumor Necrosis Factor and failure to Prevent Murine Colitis," *J. Pediatric Gastroenterology and Nutrition* 21: 410–418 (1995).

Stack et al., "The Effects of CDP571,An Engineered Human IgG 4 Anti–TNF Antibody in Crohn's Disease",*Gastroenterology*, 110:A1018 (1996).

RutGeerts et al.,"Retreatment with Anti–TNF– Chimeric Antibody (cA2) Effectively maintains cA3–Induced remission in Crohn's Disease," *Gastroenterology* 112:A1078 (1997).

Van Dullemen et al.,"Treatment of Crohn's Disease with Anti–Tumor Necrosis Factor Chimeric Monoclonal Antibody (cA2)," *Gastroenterology* 109:129–138 (1995).

Targan et al.,"A Short–Term Study of Chimeric Monoclonal Antibody cA2 to Tumor Necrosis Factor for Crohn's Disease," *New England Journal of Medicine*, 337:1029–1035 (1997).

Plevy et al.,"A Role for TNF– and Mucosal T Helper–1 Cytokines in the Pathogenesis of Crohn's Disease," *Journal of Immunology*, 6277–6282 (1997).

Sartor,"Current Concepts of the Etiology and Pathogenesis of Ulcerative Colitis and Crohn's Disease," *Inflammatory Bowel Disease*, 24:475–507 (1995).

Sartor,"Pathogenesis and Immune Mechanisms of Chronic Inflammatory Bowl Disease," *Gastroenterology*, 92:5S–11S (1997).

Robinson, "Optimizing Therapy for Inflammatory Bowel Disease," *American Journal of Gastroenterology*, 92:12–17 (1997).

Targan and Shanahan, "Pseudomembranous Colitis and Clostrridum Difficle Infection," Inflammatory Bowel Disease From Bench to Bench, 51:743–755 1994.

Ogorek and Fisher, "Differentiation Between Chrohn's Disease and Ulcerativ Colitis," in *Inflammatory Bowel Disease*, Katz, ed., 78:1249–1257 (1994).

Cameron,"Anti–TNF– treatments set to mop up in rheumatoid arthritis," *Research and Development*, pp. 9–10 (1998).

Elliott et al., "Randomised double–blind comparison of chimeric monoclonal antibody to tumour necrosis facto (cA2) in patients with rheumatoid arthritis," *Lancet* 344:1125–1127 (1994).

Gibson, "Inflammatory Bowel Disease Current Concepts in Pathogenesis and Therapy," *Clin. Immunother.*, 2(2):135–160 (1994).

(List continued on next page.)

Primary Examiner—Yvonne Eyler
Assistant Examiner—Joseph F. Murphy
(74) *Attorney, Agent, or Firm*—Medlen & Carroll, LLP

(57) ABSTRACT

Methods are described for treating inflammatory bowel disease in animals, including humans. Specific avian polyclonal antibodies directed to TNF are shown to have a beneficial effect in animal models predictive of human therapy for the treatment of colitis.

25 Claims, 1 Drawing Sheet

OTHER PUBLICATIONS

Bell and Wallace, "Infammatory Bowel Disorders Current and Future Drugs that Modulate Adhesion Molecules," *Biodrugs*, 7(4):273–284 (1997).

Opal et al., "Potential Hazards of Combination Immunotherapy in the Treatment of Experimental Septic Shock," *J. Infect. Dis.*, 173:1415–1421 (1996).

Russell et al., "Combined Inhibition of Interleukin–1 and Tumor Necrosis Factor in Rodent Endotoxemia: Improved Survival and Organ Function," *J. Infect. Dis.*, 171:1528–1538(1995).

Levine et al., "Intravenous Immunoglobulin Therapy for Active, Extensive and Medically Refractory Idiopathic Ulcerative or Crohn's Colitis" *Am J Gastroenterol.* 87:91–100 (1992).

Neurath et al., "Predominant Patholenic role of Tumor Necrosis Factor in Experimental Colitis in Mice," *Eur J Immunol* 27:1743–1750.

Neurath et al. "Antibodies to Interleukin 12 Abrogate Established Experimental Colitis in mice," *J Exp Med* 182:1281–1290 (1995).

Feldmann et al., "Cytokine Expression and Networks in Rheumatoid Arthritis: Rationale for Anti–TNFanpha Antibody Therapy and its Mechanism of Action," *J Inflamation* 47:90–96 (1996).

Reimund et al., "Increased production of tumor necrosis factor–alpha, interleukin–1–beta and interleukin–6 by morphologically normal intestinal biopsies from patients with Crohn's disease" *Gut* 39:684–689 (1996).

Duchmann et al., "Tolerance toweards resistant intestinal flora in mice is abrogated in experimental colitis and restored by treatment with interleukin–10 or antibodies to interleukin–12," *Eur J Immunol* 26:934–938 (1996).

Tsubokura et al., "Oral Administration of antibodies as prophylaxis and therapy in *Campylobacter jejuni*–infected chickens," *Clin Exp Immunol* 108:451–455 (1997).

Nicholls et al., "Cytokines in stools of children with inflammatory bowel disease or infective diarrhoea," *J Clin Path* 46:757–760 (1993).

Tjellström et al., "Oral immunoglobulin treatment in Crohn's disease," *Acta Paediatr* 86:221–223 (1997).

Rubalteli et al., "Prevention of necrotizing enterocolitis in neonates at risk by oral administration of monomeric IgG," *Dev Pharmacol Ther* 17:138–143 (1991).

Armstrong et al., "Tumor necrosis factor and inflammatory bowel disease," *British Journal of Surgery* 84:1051–1058 (1997).

Monteleone et al., "Interleukin 12 (IL–12) is expressed and actively released by Crohn's disease intestinal lamina propria mononuclear cells (LPMCs)," *Gastroenterology* 112:1169–1178 (1997).

Starnes et al., "Anti–IL–6 monoclonal antibodies protect against lethal *Escherichia coli* infection and lethal tumor necrosis factor–alpha challenge in mice" *J Immuno* 12:4185–4191 (1990).

Doherty et al., "Evidence for IFN–gama as a mediator of the lethality of endotoxin and tumor necrosis factor–alpha" *J Immuno* 5:1666–1670 (1992).

Manthey et al., "The role of cytokines in host responses to endotoxin" *Reviews in Med Microbio* 3:72–79 (1992).

Dalekos, et al., "High concentrations of soluable interleukin–2 receptors and interleukin–6 in active ulcerative cells" *Hellenic J Gastro* 8:319–327 (1995).

Evans, et al., "Treatment of ulcerative colitis with an engineered human anti–TNF–alpha antibody CDP571" *Aliment Pharmacol Ther* 11:1031–1035 (1997).

Hoang, et al., "Symposium: Role of cytokines in inflammatory bowel disease" *Acte Gastro–Enterologica Belgica* 57:219–223 (1994).

van Hogezand, et al., "Selective immunomodulation in patients with inflammatory bowel disease–future therapy or reality?" *Netherlands J of Med* 48:64–67 (1996).

Zacharchuk et al., "Macrophage–mediated cytotoxicity: Role of a soluble macrophage cytotoxic factor similar to lymphotoxin and tumor necrosis factor," *PNAS USA* 80:6341–6345 (1983).

Zacharchuk, Charles Michael, "A Macrophage Cytotoxic Factor: Immunochemical and Functional Characterization," Dissertation Abstract 1985.

Pennica et al., "Human tumor necrosis factor: precursor structure, expression and homology to lymphotoxin," *Nature* 312:724–729 (1984).

Ruff, Michael Roland, "Mechanism of Action of a Serum Oncolytic Protein, Rabbit Tumor Necrosis Factor," Dissertation Abstract. 1980.

\* cited by examiner

PREVENTION AND TREATMENT OF INFLAMMATORY BOWEL DISEASE

FIELD OF THE INVENTION

The present invention relates to therapeutics for the prevention and treatment of inflammatory bowel disease, and in particular the prevention and treatment of inflammatory bowel disease in humans as well as other animals through the use of avian polyclonal antibody therapy.

BACKGROUND OF THE INVENTION

Inflammatory bowel diseases (IBD) are defined by chronic, relapsing intestinal inflammation of obscure origin. IBD refers to two distinct disorders, Crohn's disease and ulcerative colitis (IC). Both diseases appear to result from the unrestrained activation of an inflammatory response in the intestine. This inflammatory cascade is thought to be perpetuated through the actions of proinflammatory cytolines and selective activation of lymphocyte subsets. In patients with IBD, ulcers and inflammation of the inner lining of the intestines lead to symptoms of abdominal pain, diarrhea, and rectal bleeding. Ulcerative colitis occurs in the large intestine, while in Crohn's, the disease can involve the entire GI tract as well as the small and large intestines. For most patients, IBD is a chronic condition with symptoms lasting for months to years. It is most common in young adults, but can occur at any age. It is found worldwide, but is most common in industrialized countries such as the United States, England, and northern Europe. It is especially common in people of Jewish descent and has racial differences in incidence as well. The clinical symptoms of IBD are intermittent rectal bleeding, crampy abdominal pain, weight loss and diarrhea. Diagnosis of IBD is based on the clinical symptoms, the use of a barium enema, but direct visualization (sigmoidoscopy or colonoscopy) is the most accurate test. Protracted IBD is a risk factor for colon cancer, and treatment of IBD can involve medications and surgery.

Some patients with UC only have disease in the rectum (proctitis). Others with UC have disease limited the rectum and the adjacent left colon (proctosigmoiditis). Yet others have UC of the entire colon (universal IBD). Symptoms of UC are generally more severe with more extensive disease (larger portion of the colon involved with disease).

The prognosis for patients with disease limited to the rectum proctitis) or UC limited to the end of the left colon (proctosigmoiditis) is better then that of fall colon UC. Brief periodic treatments using oral medications or enemas may be sufficient. In those with more extensive disease, blood loss from the inflamed intestines can lead to anemia, and may require treatment with iron supplements or even blood transfusions. Rarely, the colon can acutely dilate to a large size when the inflammation becomes very severe. This condition is called toxic megacolon. Patients with toxic megacolon are extremely ill with fever, abdominal pain and distention, dehydration, and malnutrition. Unless the patient improves rapidly with medication, surgery is usually necessary to prevent colon rupture.

Crohn's disease can occur in all regions of the gastrointestinal tract. With this disease intestinal obstruction due to inflammation and fibrosis occurs in a large number of patients. Granulomas and fistula formation are frequent complications of Crohn's disease. Disease progression consequences include intravenous feeding, surgery and colostomy.

Colon cancer is a known complication of chronic IBD. It is increasingly common in those patients who have had extensive IBD over many years. The risk for cancer begins to rise significantly after eight to ten years of IBD.

IBD may be treated medicinally. The most commonly used medications to treat IBD are anti-inflammatory drugs such as the salicylates. The salicylate preparations have been effective in treating mild to moderate disease. They can also decrease the frequency of disease flares when the medications are taken on a prolonged basis. Examples of salicylates include sulfasalazine, olsalazine, and mesalamine. All of these medications are given orally in high doses for maximal therapeutic benefit. These medicines are not without side effects. Azulfidine can cause upset stomach when taken in high doses, and rare cases of mild kidney inflammation have been reported with some salicylate preparations.

Corticosteroids are more potent and faster-acting than salicylates in the treatment of IBD, but potentially serious side effects limit the use of corticosteroids to patients with more severe disease. Side effects of corticosteroids usually occur with long term use. They include thinning of the bone and skin, infections, diabetes, muscle wasting, rounding of faces, psychiatric disturbances, and, on rare occasions, destruction of hip joints.

In IBD patients that do not respond to salicylates or corticosteroids, medications that suppress the immune system are used. Examples of immunosuppressants include azathioprine and 6-mercaptopurine. Immunosuppressants used in this situation help to control IBD and allow gradual reduction or elimination of corticosteroids. However, immunosuppressants render the patient immuno-compromised and susceptible to many other diseases.

Clearly there is a great need for agents capable of preventing and treating IBD. It would be desirable if such agents could be administered in a cost-effective and timely fashion, with a minimum of adverse side effects.

DEFINITIONS

The phrase "symptoms of IBD" is herein defined to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g., weight loss, fever, anemia, etc.). Some symptoms are readily determined from a blood test (e.g. anemia) or a test that detects the presence of blood (e.g., rectal bleeding). The phrase "wherein said symptoms are reduced" refers to a qualitative or quantitative reduction in detectable symptoms, including but not limited to a detectable impact on the rate of recovery from disease (e.g., rate of weight gain).

The phrase "at risk for IBD" is herein defined as encompassing the segment of the world population that has an increased risk for IBD. IBD is most commonly found in young adults, but can occur at any age. It occurs worldwide, but is most common in the United States, England, and northern Europe. It is especially common in people of Jewish descent. An increased frequency of this condition has been recently observed in developing nations.

The phrase "administered to or at the lumen" is herein defined as delivery to the space in the interior of the intestines. Such delivery can be achieved by a variety of routes (e.g., oral, rectal, etc.) in a variety of vehicles (e.g., tablet, suppository, etc.).

SUMMARY OF THE INVENTION

The present invention relates to therapeutics for the prevention and treatment of IBD. Specifically, the present invention contemplates the prevention and treatment of IBD in humans as well as other animals through the use of polyclonal antibody therapy. The examples of the present invention demonstrate a novel finding that antibodies against TNF are effective (as demonstrated in an experimental model of IBD) during the acute stage of pathogenesis. Some previous work described in the literature has suggested that the use of TNF antibodies in the acute phase of MBD is contraindicated.

In one embodiment, the present invention contemplates a method comprising the administration of polyclonal antibodies which bind to TNF. Preferably, the polyclonal antibody is reactive with TNF across species. Specifically, the present invention demonstrates that immunization with human TNF generates neutralizing antibody capable of reacting with endogenous murine TNF. Thus, the present invention provides anti-TNF antibody that will react with mammalian TNF generally. In another embodiment, the polyclonal antibodies are combined with other reagents (including but not limited to other antibodies).

In another embodiment, the present invention contemplates a method of relieving symptoms of and rescuing mammals (including humans) from episodes of acute or chronic IBD utilizing anti-TNF antibodies.

In another embodiment, the present invention contemplates a method of relieving symptoms of and rescuing mammals (including humans) from episodes of acute or chronic IBD utilizing a combination comprising anti-TNF antibodies. The present invention contemplates a method of treatment, comprising: (a) providing: i) a mammal for treatment, ii) a therapeutic preparation, comprising anti-TNF polyclonal antibodies; and (b) administering said antibodies to the lumen of said mammal.

It is not intended that the present invention be limited to specific preparations of antibodies. However, polyclonal antibodies are preferred. Most importantly, it is preferred that the antibodies not be complement fixing. More specifically, avian antibodies (e.g., chicken antibodies from eggs) are preferred.

The treatment with the antibodies has the unexpected result of reducing mortality rates in animals when administered after the onset of a chronic or acute IBD episode.

DESCRIPTION OF THE DRAWINGS

The single FIGURE.

DESCRIPTION OF THE INVENTION

Figure 1:
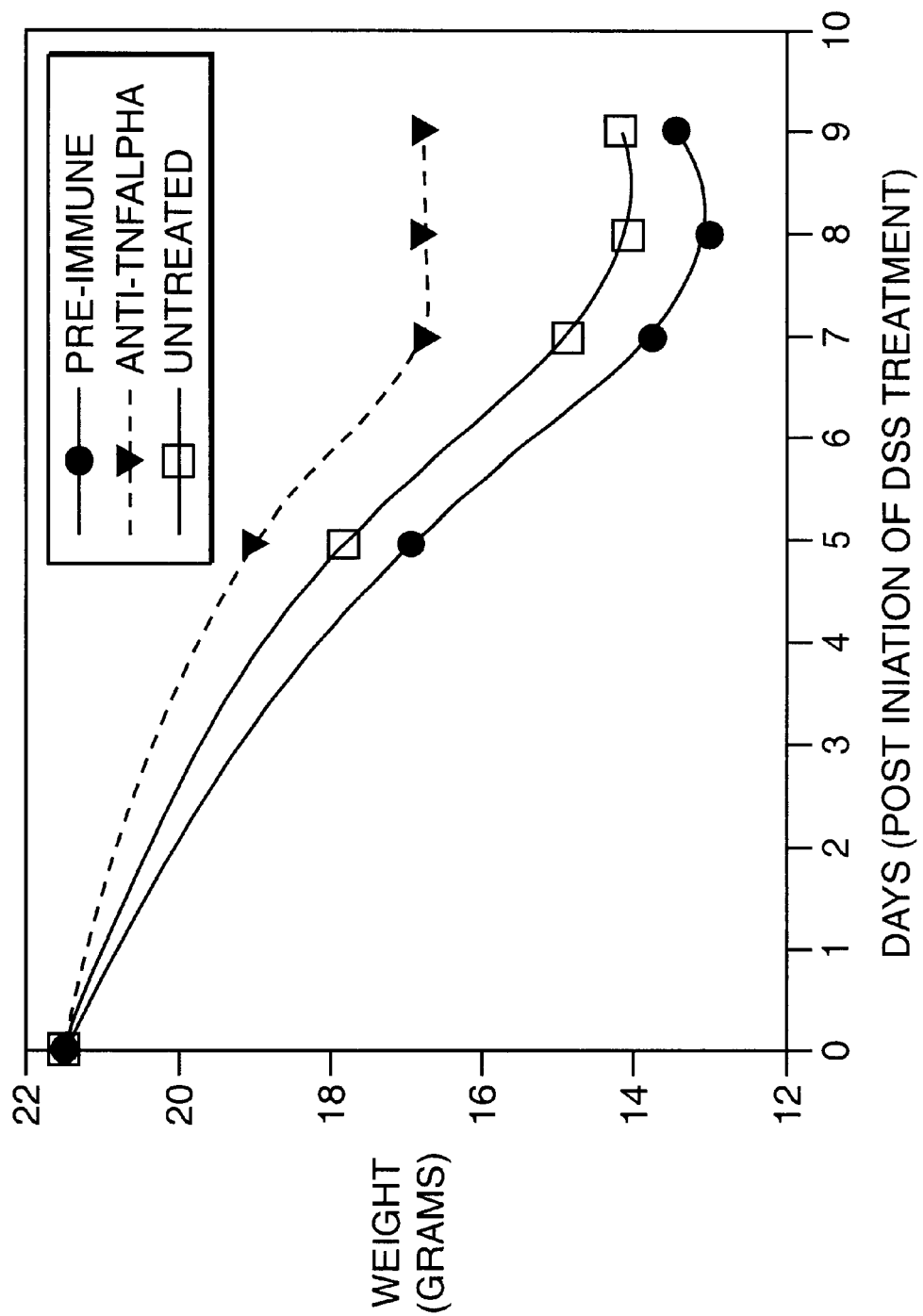
FIG. 1, shows the kinetics of body weights of mice with induced acute colitis.

The present invention relates to therapeutic compositions and methods for the prevention treatment of IBD, and in particular the prevention and treatment of IBD in humans as well as other animals.

The present invention further teaches treatments comprising anti-TNF and compositions and methods used after the onset of symptoms of IBD. As noted above, the present invention also contemplates treatment comprising anti-TNF antibody preparations. In accordance with the present invention, anti-TNF formulations are administered via intravenous, parenteral, rectal or oral route, although the present invention is not limited to these methods of administration.

It is not intended that the present invention be limited by the particular nature of a formulation or combination. The present invention contemplates combinations as simple mixtures as well as chemical hybrids. An example of the latter is where the receptor is covalently linked to a pharmaceutical such as a corticosteroid, or where two receptor types are covalently joined. Covalent binding can be accomplished by any one of many commercially available crosslinking compounds.

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as sprays (e.g. intranasal aerosols) for topical use. However, they may also be prepared either as liquid solutions or suspensions, or in solid forms. Oral formulations (e.g. for gastrointestinal inflammation) usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compositions are also prepared as injectables, either as liquid solutions or suspensions; solid forms suitable for solution in, or suspension in, liquid prior to injection may also be prepared.

The antibodies of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

EXPERIMENTAL

The following examples serve to illustrate certain preferred embodiments and aspects of the present invention and are not to be construed as limiting the scope thereof.

EXAMPLE 1

Production of Antibodies to TNF in the Hen

This example involved: (a) preparation of the immunogen and immunization; (b) purification of anti-TNF chicken antibodies from egg yolk (IgY); and (c) detection of anti-TNF antibodies in the purified IgY preparations.

(a) Preparation of the immunogen and immunization. Recombinant human Tumor Necrosis Factor Alpha, (TNF) was purchased (lyophilized without bovine serum albumin (BSA) and designated carrier-free) from R&D Systems Inc., Minneapolis, Minn. and produced in E. coli. The lyophilized TNF was reconstituted in phosphate-buffered saline pH 7.2–7.5 (PBS) at 50 µg/ml and from 2–10 µg of TNF was used to immunize each hen. Each hen received one 0.5 ml sub-cutaneous injection containing TNF with 75 µg Quil A adjuvant (Superfos Biosector, Denmark, distributed by Accurate Chem., Westbury, N.Y.) in PBS. The hens were immunized every 2 weeks for at least 3 times then placed on a maintenance immunization schedule where the hens were immunized every 4–6 weeks.

(b) Purification of anti-TNF chicken antibodies from egg yolk (IgY). Groups of eggs were collected per immunization group at least 3–5 days after the last booster immunization. The chicken yolk immunoglobulin (IgY) was extracted by a two-step polyethylene glycol (PEG) 8000 method performed according to a modification of the procedure of Polson et al., Immunol. Comm. 9:495 (1980). The yolks were separated from the whites and the yolks were placed in a graduated cylinder. The pooled yolks were blended with 4 volumes of PBS and PEG was added to a concentration of 3.5%. When the PEG was dissolved, the protein and lipid precipitates that formed were pelleted by centrifugation at 9,000×g for 15 minutes. The supernatants were decanted and filtered through 4 layers of gauze to remove the floating particulates and a second PEG step was performed by adding PEG to a final concentration of 12% (the supernatants were assumed to contain 3.5% PEG). After a second centrifugation, the supernatants were discarded and the IgY pellets were resuspended in PBS at approximately ⅙ the original yolk volume. IgYs extracted from the eggs of inmunized hens are designated as "immune IgY," while IgYs extracted from the eggs of unimmunized hens is designated "preimmune IgY." The concentration of the fractionated IgY's were estimated by measuring the absorbance at 280 nm (an optical density at 280 nm of 1.3 equals 1 mg of IgY/ml. The antibody concentrations were about 25–30 mg/ml.

(c) Detection of anti-TNF antibodies in the purified IgY preparations. In order to determine if anti-TNF response was generated and to determine relative levels of the response, enzyme-linked immunosorbent assays (ELISA) were performed. Briefly, ninety-six well Falcon Pro-bind micro-titer plates were coated overnight at 4° C. with 100 µl/well of TNF at 0.1–1.0 µg/ml PBS. The wells are then blocked with PBS containing 1% BSA and 0.05% Tween 20 and incubated for about 1 hour at 37° C. The blocking solution was removed and the immune or preimmune IgY was diluted in PBS containing BSA and the plates were incubated for 1 hour at 37° C. The plates were washed 3 times with PBS containing 0.05% Tween 20 and three times with PBS alone. Alkaline phosphatase-conjugated anti-chicken IgG was diluted 1:1000 in PBS containing 1% BSA and 0.05% Tween 20, added to the plates and incubated 1 hour at 37° C. The plates were washed as above and p-nitrophenyl phosphate at 1 mg/ml in 0.05 M $Na_2CO_3$, pH 9.5, 10 mM $MgCl_2$ was added. The plates were read in a Dynatech plate reader at 410 nm about 30 minutes after substrate addition. Good antibody titers (reciprocal of the highest immune IgY generating a signal about 3-fold higher than that of preimmune) ranging from 10,000 to 50,000 was generated.

The level of antibody response in the hens against TNF, given the low amounts of antigen used for immunization, indicates that this protein is very immunogenic in the hens and is a well-suited system to generate anti-mammalian TNF antibodies.

EXAMPLE 2

Rescue from the In Vivo Effects of Acute IBD by the Administration of Avian Polyclonal Anti-TNF Antibodies In order to determine whether anti-TNF polyclonal avian antibodies are capable of neutralizing the effects of IBD, a well-characterized and accepted murine model of IBD was utilized using dextran sodium sulfate (DSS). This model simulates UC, and the colitis induced by DSS is characterized by ulceration of the colonic mucosa, blood in the stool and weight loss. Both acute and chronic colitis can be induced in this model. To produce acute colitis, mice are treated with one DSS treatment cycle. Chronic colitis is induced by cycles of 7 days of DSS followed by 7–10 days of water for 2–7 cycles.

This example involves: (a) presentation of mice that exhibit symptoms of acute colitis; and (b) rescue from acute colitis lethality by administration of avian anti-TNF antibody subsequent to IBD onset.

(a) Acute IBD by DSS was induced in Swiss Webster mice (20–25 g), as described by I. Okayasu et al., Gastroenterology 98:694–702 (1990). Drinking water supplemented with 5% dextran sodium sulfate (M.W. 40,000; ICN Biomedicals, Inc., Aurora, Ohio) was given to the animals for 7 days. Within 3–5 days of DSS treatment, the mice began to present with bloody diarrhea, weight loss and colitis.

(b) Two experiments were performed to determine if mice could be rescued from acute colitis lethality using avian anti-TNF. Previous work using a rat anti-mouse TNF monoclonal antibody (G. Kojouharoff, et al., Clin. Exp.Immunology 107:353–358, 1997) or mouse anti-TNF polyclonal antibody (A. D. Olson, et al., J. Pediatric Gastroenterology and Nutrition 21:410–418, 1995) administered parenterally failed to protect acute colitis induced by DSS in mice. The treatment regimen in this example was performed essentially as described by Kojouharoff et al. except, the anti-TNF was administered luminally via the rectum instead of intraperitoneally.

Briefly, for therapeutic purposes in acute colitis, mice were treated twice per day with 0.1 ml. of either anti-TNF alpha or preimmune IgY containing 2–4 mg. of IgY in PBS. The mice were treated rectally using a straight 20 gauge feeding needle (Popper & Sons Inc., New Hyde Park, N.Y.) and a 1 ml syringe after light anesthesia with ether. The mice were treated from day 3 to day 7 during the DDS administration. Untreated mice with DSS induced colitis served as controls. The ability of anti TNF antibody to rescue mice from lethality associated with acute IBD is shown in Table 1. The percent of survival in each of the groups is shown 1 day after termination of DDS and antibody treatment. Note that the use of anti-TNF antibody resulted in a statistically significant increase in animal survival as compared to the untreated and Preimmune controls, with a 100% survival rate for the anti-TNF antibody administration as contrasted with the much lower 52% survival rate for the untreated animals, and 50% for the Preimmune controls.

TABLE 1

| Treatment | No. Of Survivors/No. Tested | % Survival |
| --- | --- | --- |
| Untreated | 22/42 | 52 |
| Preimmune | 5/10 | 50 |
| Anti-TNF | 10/10 | 100 |

The above experiment utilized DSS induced colitis positive mice and that were either untreated, or treated with a luminal (rectal) administration of preimmune or anti-TNF antibodies. The anti-TNF survival rate of 100% establishes conclusively a high increase in survival as compared with the 52% and 50% survival rates for both the untreated and Preimmune controls. The results of this experiment proves that avian anti-TNF antibody negates the lethal effect of IBD in vivo and strongly suggests that avian anti-TNF antibody will be useful in preventing or treating IBD.

EXAMPLE 3

Another experiment was performed to confirm the results of Example 2. The procedures used were similar, except that animal weight gain, incidence of diarrhea and presence of blood in the stool using a Hemoccult assay (Smith Kline Diagnostics, Inc., San Jose, Calif.) were monitored in addition to survival rate. The kinetics of body weights of mice with acute colitis in the treatment groups is shown in FIG. 1. In contrast to the untreated and preimmune-treated mice, body weights were generally higher and increased most rapidly in the anti-TNF treated mice. Interestingly, weight gain in mice treated parenterally with anti-TNFα was reported to be severely delayed after the end of DSS feeding. (See G. Kojouharoff, et al., *Clin. Exp.Immunology*, cited above).

Three days after the termination of DSS-treatment, stool samples were collected from mice without obvious bloody diarrhea from each group and a Hemoccult test was performed to determine blood in the stool. The results are shown in Table 2. The Hemoccult assay was not performed on mice with obvious bloody stools. These mice and mice with bloody diarrhea that died prior to the Hemoccult testing were considered Hemoccult positive and included in Table 2. The results indicate that anti-TNF IgY effectively prevented blood stools during acute colitis by DSS. In contrast, a previous report (see A. Olson et al.) indicated that anti-TNF serum administered intraperitoneally did not prevent the appearance of blood in the stool of DSS-treated mice.

Table 3 results demonstrate that anti-TNF IgY can effectively prevent mortality and morbidity (diarrhea) in the mice during acute colitis by DSS. The survival rate three days after the termination of DSS treatment in the anti-TNF treated mice was 93%, while survival rates for untreated and preimmune treated mice were 53% and 31%, respectively. In addition, diarrhea was significantly reduced in the anti-TNF treated mice compared to the untreated and preimmune-treated mice. Diarrhea was present in 87% and 92% of the untreated and preimmune treated mice (respectively) while only 21% of the anti-TNF treated mice were afflicted. The results of these treatment studies during acute colitis using DSS in mice demonstrates that luminally delivered anti-TNF antibody is an effective therapy against IBD.

TABLE 2

Anti-TNF Therapy Can Effectively Prevent Bloody Stools During Acute DSS-Induced Colitis In Mice

| Treatment | No. Of Hemocult Positive/No. Tested | % Hemocult Positive |
|---|---|---|
| Untreated | 13/15 | 87 |
| Preimmune | 12/13 | 92 |
| Anti-TNF | 3/14 | 21 |

TABLE 3

Anti-TNF Therapy Can Effectively Treat Acute DSS-Induced Colitis In Mice

| Treatment | No. Of Survivors/No. Tested | % Survival | % Diarrhea |
|---|---|---|---|
| Untreated | 8/15 | 53 | 87 |
| Preimmnune | 4/13 | 31 | 92 |
| Anti-TNF | 13/14 | 93 | 21 |

Those skilled in the art will know, or be able to ascertain upon review of the above, using no more than routine experimentation, many equivalents to the specific embodiments of the invention described herein. These and all other equivalents are intended to be encompassed by the following claims.

What is claimed is:

1. A method of treatment, comprising:
   a) providing:
      i) a mammal with a symptom of inflammatory bowel disease,
      ii) a therapeutic formulation comprising polyclonal antibodies directed to TNF, and;
   b) administering said formulation to the lumen of the intestine of said mammal, wherein said administering is performed orally under conditions such that said symptom is reduced.

2. The method of claim 1, wherein said mammal is a human.

3. The method of claim 1, wherein said polyclonal antibodies are avian antibodies.

4. The method of claim 3, wherein said avian antibodies are chicken antibodies.

5. The method of claim 4, wherein said chicken antibodies are derived from chicken eggs.

6. A method of treatment, comprising:
   a) providing:
      i) a human patient with symptoms of inflammatory bowel disease,
      ii) a therapeutic formulation comprising avian polyclonal antibodies directed to TNF, and;
   b) administering said formulation to the lumen of the intestine of said patient.

7. The method of claim 6, wherein said human is a child.

8. The method of claim 6, wherein said administering reduces said symptoms.

9. The method of claim 6, wherein said administering is performed orally.

10. The method of claim 6, wherein said administering is performed rectally.

11. The method of claim 6, wherein said human has symptoms of ulcerative colitis.

12. The method of claim 6, wherein said avian polyclonal antibodies are chicken antibodies.

13. The method of claim 12, wherein said chicken antibodies are purified antibodies.

14. The method of claim 13, wherein said chicken antibodies are purified from chicken eggs.

15. A method of treatment, comprising:
   a) providing:
      i) a human patient with a symptom of inflammatory bowel disease,
      ii) a therapeutic formulation comprising polyclonal antibodies directed to TNF, and;
   b) administering said formulation to the lumen of the intestine of said patient, wherein said administering is performed rectally under conditions such that said symptom is reduced.

16. The method of claim 15, wherein said administering reduces said symptoms.

17. The method of claim 15, wherein said avian antibodies are chicken antibodies.

18. The method of claim 17, wherein said chicken antibodies are purified antibodies.

19. The method of claim 18, wherein said chicken antibodies are purified from chicken eggs.

20. A method of treatment, comprising:
a) providing:
i) a mammal at risk for inflammatory bowel disease,
ii) a therapeutic formulation comprising polyclonal antibodies directed to TNF, and;
b) orally administering said formulation to the lumen of the intestine of said mammal, prior to the onset of inflammatory bowel disease.

21. The method of claim 20, wherein said human is a child.

22. The method of claim 20, wherein said antibodies are chicken antibodies.

23. The method of claim 22, wherein said chicken antibodies are purified antibodies.

24. The method of claim 23, wherein said chicken antibodies are purified from chicken eggs.

25. A method of treatment, consisting of:
a) providing:
i) a mammal with a symptom of inflammatory bowel disease,
ii) a therapeutic formulation comprising polyclonal antibodies directed to TNF, and;
b) administering said formulation to the lumen of the intestine of said mammal, wherein said administering is performed orally under conditions such that said symptom is reduced.

* * * * *